(12) United States Patent
Böhl et al.

(10) Patent No.: US 10,481,054 B2
(45) Date of Patent: Nov. 19, 2019

(54) METHOD AND AUTOMATIC MACHINE FOR EMBEDDING A TISSUE SAMPLE INTO AN EMBEDDING MEDIUM

(71) Applicant: LEICA BIOSYSTEMS NUSSLOCH GMBH, Nussloch (DE)

(72) Inventors: Florian Böhl, Neckargemünd (DE); Ralf Eckert, Schriesheim (DE); Karin Flieger, Seeheim-Jugendheim (DE); Markus Berberich, Heidelberg (DE); Hermann Ulbrich, Bad Schönborn (DE); Stella Knorr, Brighton (AU); Andrew Guy, Coburg (AU)

(73) Assignee: Leica Biosystems Nussloch GmbH, Nussloch (DE)

( * ) Notice: Subject to any disclaimer, the term of this patent is extended or adjusted under 35 U.S.C. 154(b) by 263 days.

(21) Appl. No.: 15/254,211

(22) Filed: Sep. 1, 2016

(65) Prior Publication Data
US 2017/0067804 A1 Mar. 9, 2017

(30) Foreign Application Priority Data
Sep. 4, 2015 (DE) .................. 10 2015 114 893

(51) Int. Cl.
*G01N 1/36* (2006.01)
(52) U.S. Cl.
CPC ......... *G01N 1/36* (2013.01); *G01N 2001/364* (2013.01); *G01N 2001/366* (2013.01)
(58) Field of Classification Search
CPC ........................... G01N 1/36; G01N 2001/366
See application file for complete search history.

(56) References Cited

U.S. PATENT DOCUMENTS

2008/0254504 A1 10/2008 Vom et al.
2010/0151513 A1 6/2010 Vom et al.
(Continued)

FOREIGN PATENT DOCUMENTS

DE 102009035019 2/2011
DE 102013204648 9/2014
(Continued)

OTHER PUBLICATIONS

Wax Glossary, Petroleum products Glossary, Webage, May 15, 2018.*
(Continued)

*Primary Examiner* — Kara D Johnson
(74) *Attorney, Agent, or Firm* — Hodgson Russ LLP

(57) ABSTRACT

The invention relates to a method for embedding a tissue sample into an embedding medium. In a first step the tissue sample is held in an intended orientation in a container by means of a holding element that presses the tissue sample against a base of the container. In a further step a liquid embedding medium that has a temperature above 64 degrees Celsius, in particular in the range from 65 degrees Celsius to 67 degrees Celsius, or a temperature of 66 degrees Celsius, is poured into the container, and the base of the container is cooled. In a further step a separating motion is executed by way of which the tissue sample and the holding element move away from each other, those layers of the embedding medium through which the holding element moves during the separating motion having, during the separating motion, temperatures in the range from 54 degrees Celsius to 64 degrees Celsius, in particular of 60 degrees Celsius, and/or those portions of the embedding medium which are directly adjacent to the holding element having, during the separating motion, a temperature in the range from 54 degrees
(Continued)

Figure 1:
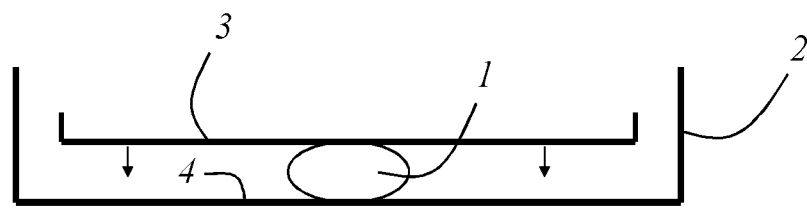

Celsius to 64 degrees Celsius, in particular of 60 degrees Celsius.

25 Claims, 2 Drawing Sheets

(56) References Cited

U.S. PATENT DOCUMENTS

| | | | |
|---|---|---|---|
| 2014/0027407 A1 | 1/2014 | Deshpande et al. | |
| 2014/0186883 A1* | 7/2014 | Eckert | G01N 1/28 435/40.52 |
| 2014/0273083 A1 | 9/2014 | Knorr et al. | |
| 2014/0273084 A1 | 9/2014 | Boehl et al. | |
| 2015/0160104 A1 | 6/2015 | Berberich | |

FOREIGN PATENT DOCUMENTS

| | | |
|---|---|---|
| DE | 102013204649 | 9/2014 |
| DE | 102013204651 | 9/2014 |
| DE | 102013225397 | 6/2015 |
| EP | 2322938 | 1/2013 |

OTHER PUBLICATIONS

Protocols Online. Paraffin Processing of Tissue [online]. Jul. 15, 2012 [retrieved May 14, 2019]. Retrieved from the Internet: <URL: https://web.archive.org/web/20130811092921/https://www.protocolsonline.com/histology/sample-preparation/paraffin-processing-of-tissue/>. (Year: 2012).*

"Automatically". Dictionary [online]. Lexico , 2019 [retrieved on Aug. 6, 2019]. Retrieved from the Internet<URL:: https://www.lexico.com/en/definition/automatically>. (Year: 2019).*

Goodwin College Online Studies, Histology: Embedding Process, video, online, available at: https://www.youtube.com/watch?v=xlyXA3c3oxU May 20, 2014.

Leica Biosystems, Safety Data Sheet Blue Ribbon Paraffin, pp. 1-7 Aug. 22, 2013.

Polysciences Inc., Histology Product Guide, pp. 1-16 Aug. 13, 2014.

Winsor, Leigh, Tissue Processing, Laboratory Hispathology: A Complete Reference, Section 4.2, pp. 1-42 Jan. 1, 1994.

Leica Biosystems, Leica EG1150, Product Brochure, pp. 1-8 Oct. 1, 2012.

Leica Biosystems, Leica EG1160, Manual, pp. 1-32 May 1, 2001.

Leica Biosystems, Leica HistoCore Arcadia H, Manual, pp. 1-50 Jul. 1, 2015.

DIAPATH, DIAPATH Tissue Embedding Station, Product Brochure, pp. 1-2 Date Unknown.

MEDITE, TES Valida Modular Paraffin Embedding Center, Product Brochure, pp. 1-4 Date Unknown.

Thermo Scientific, Thermo Scientific Anatomical Pathology, Product Catalog, pp. iv, v, 6-8, 13, 21, 22, 91 Jan. 1, 2011.

National Institute of Open Schooling, Embedding, Diploma in Medical Laboratory Technology, Histology and Cytology Module, Lesson 8, pp. 42-49 Aug. 4, 2014.

G.RAU GmbH, Thermal Actuators, Product Brochure, pp. 1-11 Date Unknown.

* cited by examiner

METHOD AND AUTOMATIC MACHINE FOR EMBEDDING A TISSUE SAMPLE INTO AN EMBEDDING MEDIUM

CROSS-REFERENCE TO RELATED APPLICATIONS

The present application claims priority of German Application No. 10 2015 114 893.5 filed Sep. 4, 2015, the entirety of which is incorporated herein by reference.

FIELD OF THE INVENTION

The invention relates to a method for embedding a tissue sample into an embedding medium.

The invention furthermore relates to an automatic machine for executing such a method and to the use in the execution of such a method of a tissue cassette which comprises a container having a base, and which comprises a holding element for holding at least one tissue sample on the base.

BACKGROUND OF THE INVENTION

The manner in which a biological tissue sample is to be processed for a histological investigation is known. Firstly, trimming of the tissue sample and introduction into a cassette are accomplished. The sample is then prepared, by way of a plurality of chemical treatments, for microscopic investigation. In this context the sample is first fixed with a fixing medium, the water present in the sample is removed, and optionally further processing steps are completed. Infiltration of an infiltration medium, usually paraffin, into the sample comes at the end of this multi-step process.

The sample is then embedded, usually manually, into an embedding medium, for example paraffin. For this the sample is placed into a mold and the mold is filled with the initially liquid embedding medium. The embedding medium then hardens. The result is to produce an embedded block in which the sample is surrounded and immobilized in stationary fashion by the embedding medium.

After hardening of the embedding medium, the embedded block that contains the sample can be sectioned with the microtome into individual thin sample sections that are stained in a subsequent step and can then be investigated with a microscope. It is important for this purpose that the tissue sample have a specific orientation within the embedded block, in particular in order to ensure proper sectioning and to ensure that the tissue sample can be sectioned along the sample layers that are of interest for microscopic investigation.

In order to allow automation of the embedding process, it is necessary for the tissue sample to maintain its intended orientation relative to the molding vessel during the embedding operation. If a holding element that holds the tissue sample in its orientation is used, the problem exists that the holding element necessarily becomes embedded together with the tissue sample, and impedes subsequent generation of sample sections and/or even damages the microtome blade.

EP 2 322 938 B1 discloses an automated machine that is embodied for embedding tissue samples that must be arranged on very special carriers. The carriers are suitable for being sectioned together with the embedded sample by means of a microtome. The machine comprises several immovable holders, each holder being embodied to hold one of the special carriers during the entire embedding operation. Once a carrier equipped with a sample has been positioned in a holder, the carrier is filled with an embedding medium that is delivered from a dispenser. The carrier is then cooled by the carrier, which is also embodied as a cooling unit in order to implement an additional function.

Instead of a sectionable carrier it is also possible to use a special tissue cassette such as the one known from DE 10 2013 204 651 A1. This document describes an embedding process in which a special sectionable carrier is not necessary. In this embedding process, paraffin is poured into the tissue cassette and the tissue cassette is then held against a cooling surface so that the paraffin at the bottom of the tissue cassette begins to cool. As a result of the paraffin cooling in this region, a first thin layer of solidified paraffin adheres the tissue sample to the base. While the remaining paraffin is still molten, a retraction component pulls a first tissue engagement surface away from the tissue sample.

DE 10 2013 204 651 A1 concretely discloses a tissue cassette for holding a tissue sample, which comprises a retention component that has a first tissue engagement surface, and at least one preload element. The first tissue engagement surface is mounted on the retention component movably thanks to the preload element. A base comprises a second tissue engagement surface and is embodied so that it engages into the retention component in order to embody an interior space region, the first and the second tissue engagement surface facing toward one another. The preload element is configured so that it forces the first tissue engagement surface toward the second tissue engagement surface in order to retain the tissue sample between them in the interior space region. A retraction component is connected to the retention component and is embodied so that it retracts the first tissue engagement surface and compresses the preload element in order to form a gap between the tissue sample and either the first tissue engagement surface or the second tissue engagement surface.

The use of a tissue cassette of this kind is not unproblematic in practice, however, since a large number of interfering phenomena can occur which can in fact cause the tissue sample to become unusable. For example, it can happen that the tissue sample becomes inadvertently moved or damaged in the context of the retraction operation, or even that the tissue engagement surface cannot be retracted sufficiently or at all.

SUMMARY OF THE INVENTION

The object of the present invention is therefore to describe a method that is executable in automated fashion and that enables reliable generation of an embedded block in which a tissue sample exhibits a predefined orientation.

The object is achieved by a method that is characterized by the following steps:
a. holding the tissue sample in an intended orientation in a container by means of a holding element that presses the tissue sample against a base of the container;
b. pouring into the container a liquid embedding medium that has a temperature above 64 degrees Celsius, in particular in the range from 65 degrees Celsius to 67 degrees Celsius, or a temperature of 66 degrees Celsius;
c. cooling the base of the container;
d. executing a separating motion by way of which the tissue sample and the holding element move away from each other, those layers of the embedding medium through which the holding element moves during the separating motion having, during the separating motion, temperatures in the range from 54 degrees Celsius to 64 degrees Celsius, in particular of 60 degrees Celsius, and/or those portions of the embedding medium which are directly adjacent to the holding element having, during the separating motion, a temperature in the range from 54 degrees Celsius to 64 degrees Celsius, in particular of 60 degrees Celsius.

The invention has the very particular advantage that on the one hand retention of the tissue sample in its orientation relative to the container is always ensured, and on the other hand there is simultaneously a guarantee that the holding element can be removed without sticking in the embedding medium and without modifying the position of the tissue sample or even damaging it.

What has been recognized according to the present invention is that those portions of the embedding medium which are adjacent to the cooled base have already hardened sufficiently to hold the tissue sample in its position and orientation if the temperature of the embedding medium at the location of the holding element is still in the range from 54 degrees Celsius to 64 degrees Celsius, in particular is 60 degrees Celsius, so that the holding element can be removed from the tissue sample. In this temperature range the embedding medium is still sufficiently liquid that the holding element can be removed without disruption, and in particular without influencing the position or orientation of the tissue sample, or damaging it, or negatively influencing the quality of the hardening process. In particular, provision can advantageously be made that the embedding medium has, during execution of the separating motion, an average temperature in the range from 54 degrees Celsius to 64 degrees Celsius, in particular of 60 degrees Celsius.

Execution of the individual method steps at temperatures recited above is advantageous in particular when paraffin is used as an embedding medium, in particular when the paraffin has a drop point in the range from 50 degrees Celsius to 60 degrees Celsius. The temperatures at which the individual method steps are executed can be correspondingly adapted if embedding media having different drop points are used.

In particular, provision can advantageously be made that the separating motion is activated, in particular automatically, as soon as the layer of embedding medium directly adjacent to the base has reached a temperature of 52 degrees Celsius. It has been recognized according to the present invention that this is the case when the temperature of the embedding medium at the location of the holding element is in the range from 54 degrees Celsius to 64 degrees Celsius, in particular is 60 degrees Celsius.

Once the separating motion has been completely executed, the embedding medium is allowed to cool further until it has completely hardened and the resulting embedded block can be removed from the container.

In a particularly advantageous embodiment the holding element is not completely removed from the embedding medium. The separating motion can instead advantageously end while the holding element is still located inside the embedding medium. The holding element is thus also embedded. An embodiment of this kind has the very particular advantage that the holding element imparts additional mechanical stability to the embedded block that results from cooling of the embedding medium. The result is, advantageously, to prevent the embedded block from becoming unintentionally deformed upon subsequent clamping and/or upon sectioning with a microtome. It is also possible to use, for clamping, projections that are connected to the holding element and project out of the embedded block. The fact that the holding element has been moved away from the tissue sample by means of the separating motion, however, at the same time advantageously ensures that the stabilizing holding element does not need to be cut into when tissue sections are produced.

The invention is not limited to embedding a single tissue sample in each case. It is instead also possible to embed several tissue samples simultaneously in the same container in the manner described. When it is stated in the context of this Application that "a tissue sample" is being embedded, this serves merely for simpler explanation of the invention with no intention to associate any limitation therewith.

The embedding medium can, for example, be paraffin or can contain, in particular predominantly, paraffin.

In a very particularly advantageous embodiment of the method the embedding medium, in particular when it is paraffin having a drop point in the range from 50 degrees Celsius to 60 degrees Celsius, has a temperature above 64 Celsius upon pouring. This ensures that the embedding medium fills up the entire available space inside the container before it cools. A pouring temperature in the range from 65 to 67 degrees Celsius, in particular a temperature of 66 degrees Celsius, is particularly advantageous. Such a temperature ensures that the tissue sample is reliably surrounded on all sides with the embedding medium. In addition, the time interval required for hardening of the embedding medium in the region of the base, and then for complete hardening in the remaining regions, is particularly short. High throughput rates are thereby achieved so that a particularly large number of tissue samples can be embedded, for example by an automatic machine, per unit time.

The drop point can differ for embedding media of different types. For example, there are embedding media that have a drop point in the range from 52 degrees Celsius to 58 degrees Celsius, which is described e.g. in DE 10 2009 035 019 A1. It is therefore very generally advantageous if the embedding medium has, upon pouring, a temperature that is at least 4 degrees Celsius above the drop point of the embedding medium. In particular, provision can advantageously be made that upon pouring, the embedding medium has a temperature that is 5 to 7 degrees Celsius above the drop point of the embedding medium, and/or that is 6 degrees Celsius above the drop point of the embedding medium. For example, an embedding medium that has a drop point of, for example, 55 degrees Celsius can advantageously be poured in, in particular, at a temperature of 61 degrees Celsius.

As will be explained by way of example below, there are various possibilities regarding how and, in particular, when the separating motion can be initiated.

For example, provision can advantageously be made that the separating motion is activated, in particular automatically, when a predefined or predefinable activation temperature of the embedding medium or of the container or of the holding element is reached. It is possible for this purpose, for example, to measure the temperature directly with a temperature sensor. Alternatively, it is also possible to infer the temperature via another parameter, in order to ascertain thereby whether the activation temperature has been reached. It is possible in particular to infer the temperature of the embedding medium or of the container or of the holding element by way of the time interval since the beginning of the cooling operation at the base. In particular, a calibration measurement can have been carried out here before the method is carried out, in order to ascertain the time period after which the activation temperature is present.

The length of the time period can depend in particular on the nature and size of the container and on the nature of the embedding medium.

It is also possible for a holding mechanism that moves the holding element to comprise at least one shape memory component. The shape memory component is advantageously embodied in such a way that it automatically retracts the holding element as soon as the shape memory component is at the activation temperature.

The holding element can advantageously be embodied, for example, as a sieve. A holding element embodied in this way has the advantage that the embedding medium can flow through the sieve openings during the separating motion. The advantageous result thereof is that turbulence in the embedding medium, which could negatively influence the orientation of the tissue sample, is largely avoided during the separating motion. An embodiment of this kind moreover has the further advantage that less resistance is presented to the separating motion, and the risk of sticking of the holding element is decreased.

The holding element can be moved in a wide variety of ways in order to execute the separating motion. For example, it is possible to exert a force on the holding element by means of a magnet. For this purpose the holding element can be made at least in part of a magnetic material. It is also possible to move the holding element horizontally and/or vertically by means of a gripper. The gripper can be embodied, for example, as a hook that hooks onto the holding element for execution of the separating motion. As already mentioned, provision can also be made that for execution of the separating motion, the holding element is moved by means of a holding mechanism that comprises a shape memory component, for example based on memory polymers.

As already mentioned, provision can advantageously be made that the point in time of the beginning of cooling is utilized as a time base, and the separating motion begins immediately after expiration of a predefined or predefinable time period after the beginning of cooling, and/or that the separating motion is automatically started immediately after expiration of a predefined or predefinable time period after the beginning of cooling. Particularly good results are achieved when the time period between the beginning of cooling and the beginning of the separating motion is in the range from 1 second to 4 seconds or in the range from 2 seconds to 3 seconds.

In particular in order to ensure that the holding element is not unintentionally stopped, before completion of the separating motion, in the cooling and increasingly solidifying embedding medium, the separating motion should proceed within a predefined or predefinable time window and/or should last for a predefined or predefinable time period. Particularly good results are achieved when the time window is 17 to 20 seconds long and/or when the time period lasts 17 to 20 seconds.

Cooling of the base of the container can advantageously be effected, for example, by the fact that the container is brought into thermally conductive contact with a cooling element. The cooling element can be, for example, a cooling plate onto which the container is placed.

In order to carry out the method it is possible, for example, firstly to pour the embedding medium into the container and then to cool the base of the container, for example by effecting contact with a cooling plate. In such an embodiment the moment at which contact is effected can be utilized as a starting point in time for the time period after whose expiration the separating motion is started. Alternatively, it is also possible firstly to cool the container on the base, for example by effecting contact with a cooling plate, and then to pour in the embedding medium. In this case the point in time of pouring, in particular the point in time at which the pouring operation ends, can be utilized as a starting point in time for a time period after whose expiration the separating motion is started.

In a very particular advantageous embodiment the container is cooled exclusively at the base. Such an embodiment has the very particular advantage that stress cracks within the cooled embedding medium are effectively avoided.

As already mentioned, the method according to the present invention can be used in particular in automated processing of tissue samples. It is possible in particular in this context for a plurality of tissue samples, which are retained in a plurality of containers in which the tissue samples are held in their respective target orientations, to be embedded simultaneously. In this context, for example, several containers can respectively be retained respectively in a common holder, for example in matrix fashion and in coplanar fashion in one plane. Such a holder can, for example, easily be placed on a cooling plate so that the several containers can respectively be simultaneously cooled at their base. It is also possible, however, for example, to use a holder in which the containers are arranged in a stack arrangement. With such an embodiment, for example, several cooling fingers could be provided which engage into the interstices between the containers in order to cool each of the individual containers from below at their base. The use of a holder for several containers has the advantage that an automatic machine, by handling the common holder, can simultaneously transport several containers, fill them with an embedding medium, and cool them; this increases the throughput rate.

The method according to the present invention can also, in particular, be a constituent of a higher-order method for processing a tissue sample or several tissue samples, in which in addition to embedding, further process steps are also previously or subsequently executed. The further process steps can in particular involve fixing the tissue sample with at least one fixing agent prior to embedding, and/or infiltrating at least one infiltration medium, in particular paraffin, into the tissue sample. Provision can be made here in particular that the further process steps are also carried out after the tissue sample has been arranged in its intended orientation in the container. The tissue sample thus remains in the same container during embedding and during at least one preceding further process step, until it is completely embedded.

It is particularly advantageous to use a tissue cassette which comprises a container having a base, and which comprises a holding element for holding at least one tissue sample on the base, for execution of the method according to the present invention.

BRIEF DESCRIPTION OF THE DRAWING VIEWS

Figure 6:
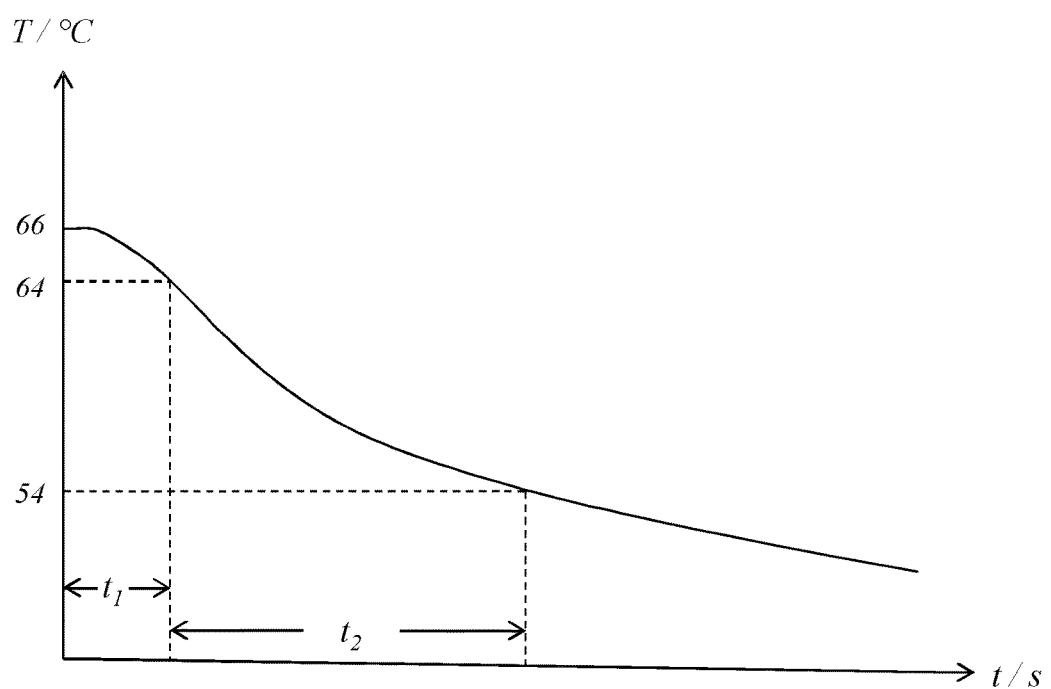

The subject matter of the invention is depicted schematically and by way of example in the drawings and will be described below with reference to the Figures, identical or identically functioning elements usually being labeled with the same reference characters. In the Figures:

FIGS. 1 to 5 illustrate the steps in accordance with an exemplifying embodiment of the method according to the present invention; and FIG. 6 is an illustration of the change over time in the temperature of an embedding medium poured into a container, and an illustration of the relevant time periods in the context of carrying out an exemplifying embodiment of the method according to the present invention.

DETAILED DESCRIPTION OF THE INVENTION

FIG. 1 illustrates the situation in the context of a first step for executing an exemplifying embodiment of the method according to the present invention. A tissue sample 1 is retained in an intended orientation in a container 2 by means of a holding element 3 that presses tissue sample 1 against a base 4 of container 2. Holding element 3 can be embodied, for example, as a spring-loaded sieve. The fact that tissue sample 1 is clamped between holding element 3 and base 4 ensures that tissue sample 1 retains its intended orientation.

Figure 2:
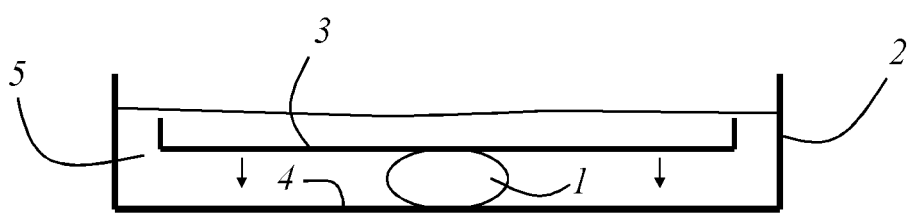

In a following step a liquid embedding medium 5, which in particular can be paraffin and which has a temperature above 64 degrees Celsius, in particular in the range from 65 degrees Celsius to 67 degrees Celsius or a temperature of 66 degrees Celsius, is poured into the container, as illustrated in FIG. 2. During this step, holding element 3 continuously holds tissue sample 1 in its position and intended orientation.

Figure 3:
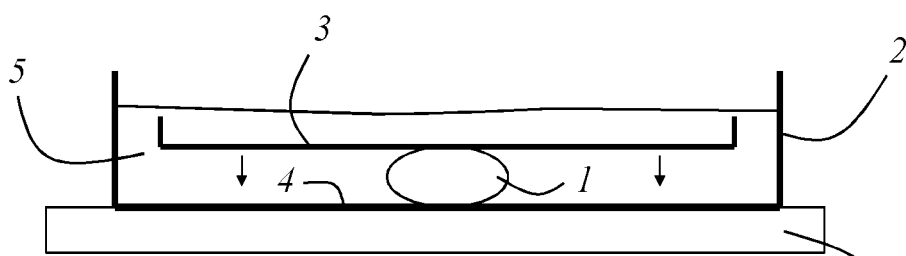

In a following step, cooling of base 4 of container 2 is accomplished by bringing base 4 into contact with a cooling element 6; this is illustrated in FIG. 3. In this example cooling element 6 is embodied as a cooling plate on which container 2 is placed. During this step as well, holding element 3 continuously holds tissue sample 1 in its position and intended orientation.

Figure 4:
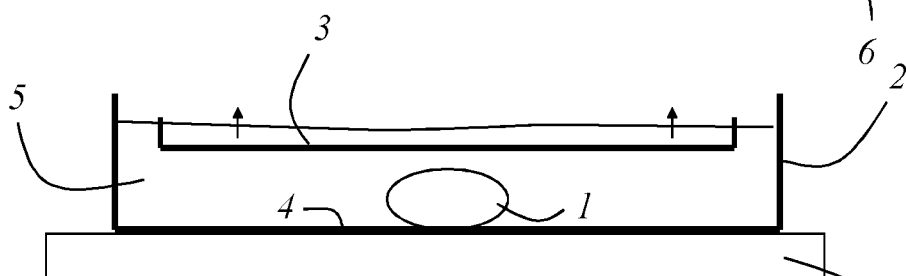
Figure 5:
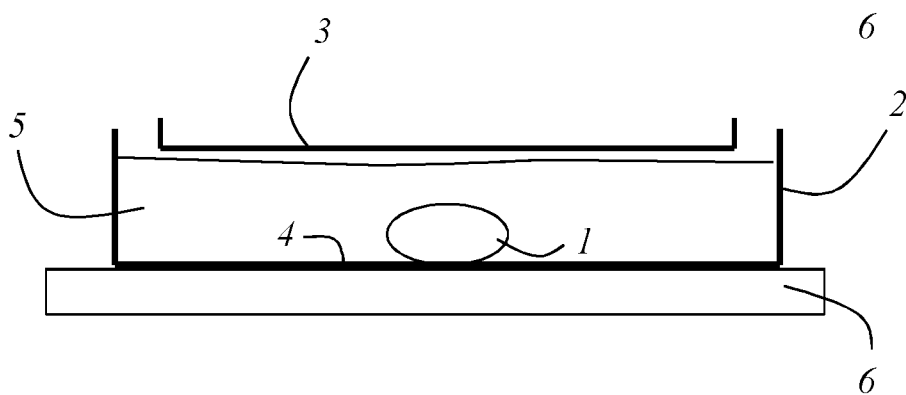

As soon as that layer of embedding medium 5 in which holding element 3 is located has a temperature in the range from 54 degrees Celsius to 64 degrees Celsius, in particular of 60 degrees Celsius, a separating motion is started by means of which tissue sample 1 and holding element 3 move away from one another, this being depicted in FIG. 4. In this situation, embedding medium 5 in the region of the base has already cooled, and thereby hardened, sufficiently to hold tissue sample 1 in its position and orientation, so that holding by means of holding element 3 has become unnecessary. In order to ensure that holding element 3 does not become stuck in the cooling and increasingly solidifying embedding medium 5 before completion of the separating motion, the separating motion is completed within a predefined time window of 17 to 20 seconds.

Embedding medium 5 can then continue to cool until it is completely hardened and the resulting embedded block, together with the embedded tissue sample 1, can be removed from container 2.

FIG. 6 shows the change over time in the temperature of embedding medium 5 initially having a temperature of 66 degrees Celsius, in the region of holding element 3 after the beginning of cooling (t=0) of base 4, and illustrates the relevant time periods in the context of carrying out an exemplifying embodiment of the method according to the present invention.

In this exemplifying embodiment the separating motion begins immediately after expiration of a first time period $t_1$ following the beginning of cooling (t=0). Particularly good results are achieved when the first time period $t_1$ is in the range from 1 second to 4 seconds or in the range from 2 seconds to 3 seconds.

In particular in order to ensure that holding element 3 does not become unintentionally immobilized in the cooling and increasingly solidifying embedding medium 5 prior to completion of the separating motion, the separating motion should take place and be completed within a second time period $t_2$ immediately subsequent to the first time period $t_1$. Particularly good results are achieved when the second time period $t_2$ is 17 to 20 seconds long.

PARTS LIST

1 Tissue sample
2 Container
3 Holding element
4 Base
5 Embedding medium
6 Cooling element
$t_1$ First time period
$t_2$ Second time period

What is claimed is:

1. A method for embedding a tissue sample (1) into an embedding medium, comprising:
   a. holding the tissue sample (1) in an intended orientation in a container (2) by means of a holding element (3) that presses the tissue sample (1) against a base (4) of the container (2);
   b. pouring into the container (2) a liquid embedding medium (5) that has a temperature above 64 degrees Celsius;
   c. cooling the base (4) of the container (2);
   d. executing a separating motion by way of which the tissue sample (1) and the holding element (3) move away from each other, the embedding medium (5) through which the holding element (3) moves during the separating motion having, during the separating motion, temperatures in the range from 54 degrees Celsius to 64 degrees Celsius, and/or those portions of the embedding medium (5) which are directly adjacent to the holding element (3) having, during the separating motion, a temperature in the range from 54 degrees Celsius to 64 degrees Celsius; wherein
   e. the separating motion begins automatically when a predefined or predefinable activation temperature of the embedding medium (5) or of the container (2) or of the holding element (3) is reached: and/or
   f. the separating motion is automatically activated when a predefined or predefinable activation temperature of the embedding medium (5) or of the container (2) or of the holding element (3) is reached.

2. The method according to claim 1, wherein the embedding medium (5), upon pouring, has a temperature in the range from 65 degrees Celsius to 67 degrees Celsius.

3. The method according to claim 2, wherein the embedding medium (5), upon pouring, has a temperature of 66 degrees Celsius.

4. The method according to claim 1, wherein those layers of the embedding medium (5) through which the holding element (3) moves during the separating motion have, during the separating motion, a temperature of 60 degrees Celsius, and/or those portions of the embedding medium (5) which are directly adjacent to the holding element (3) have, during the separating motion, a temperature of 60 degrees Celsius.

5. The method according to claim 1, wherein the embedding medium (5) has, during execution of the separating motion, an average temperature in the range from 54degrees Celsius to 64 degrees Celsius.

6. The method according to claim 5, wherein the embedding medium (5) has, during execution of the separating motion, an average temperature of 60 degrees Celsius.

7. The method according to claim 1, wherein the embedding medium (5) contains paraffin.

8. The method according to claim 7, wherein the embedding medium (5) contains a greater amount of paraffin than any other ingredient.

9. The method according to claim 8, wherein the embedding medium (5) is paraffin.

10. The method according to claim 1, wherein the embedding medium (5), upon pouring, has a temperature that is at least 4 degrees Celsius above a drop point of the embedding medium.

11. The method according to claim 10, wherein the embedding medium (5), upon pouring, has a temperature that is 5 to 7 degrees Celsius above the drop point of the embedding medium.

12. The method according to claim 11, wherein the embedding medium (5), upon pouring, has a temperature that is 6 degrees Celsius above the drop point of the embedding medium.

13. The method according to claim 1, wherein
 a. the temperature of the embedding medium (5) or of the container (2) or of the holding element (3) is measured with a temperature sensor; or
 b. the temperature of the embedding medium (5) or of the container (2) or of the holding element (3) is measured with a temperature sensor and the separating motion is activated automatically as soon as the measured temperature reaches the activation temperature.

14. The method according to claim 1, wherein a holding mechanism that moves the holding element (3) comprises at least one shape memory component.

15. The method according to claim 1, wherein the separating motion occurs within a predefined or predefinable time window and/or lasts for a predefined or predefinable time period ($t_2$).

16. The method according to claim 15, wherein the time window is 17 to 20 seconds long; and/or the time period ($t_2$) lasts 17 to 20 seconds.

17. The method according to claim 1, wherein the container (2) is cooled exclusively at the base (4); and/or the base (4) is cooled by the fact that the container (2) is brought into thermally conductive contact with a cooling element.

18. A method for embedding a tissue sample (1) into an embedding medium, comprising:
 a. holding the tissue sample (1) in an intended orientation in a container (2) by means of a holding element (3) that presses the tissue sample (1) against a base (4) of the container (2);
 b. pouring into the container (2) a liquid embedding medium (5) that has a temperature above 64 degrees Celsius;
 c. cooling the base (4) of the container (2);
 d. executing a separating motion by way of which the tissue sample (1) and the holding element (3) move away from each other, the embedding medium (5) through which the holding element (3) moves during the separating motion having, during the separating motion, temperatures in the range from 54 degrees Celsius to 64 degrees Celsius, and/or those portions of the embedding medium (5) which are directly adjacent to the holding element (3) having, during the separating motion, a temperature in the range from 54 degrees Celsius to 64 degrees Celsius, wherein
 e. the separating motion begins immediately after expiration of a predefined or predefinable time period ($t_1$) after the beginning of cooling; and/or
 f. the separating motion is automatically started immediately after expiration of a predefined or predefinable time period ($t_1$) after the beginning of cooling.

19. The method according to claim 18, wherein the time period between the beginning of cooling and the beginning of the separating motion is in the range from 1 second to 4 seconds.

20. The method according to claim 19, wherein the time period between the beginning of cooling and the beginning of the separating motion is in the range from 2 seconds to 3 seconds.

21. A method for embedding a tissue sample (1) into an embedding medium, comprising:
 a. holding the tissue sample (1) in an intended orientation in a container (2) by means of a holding element (3) that presses the tissue sample (1) against a base (4) of the container (2);
 b. pouring into the container (2) a liquid embedding medium (5) that has a temperature above 64 degrees Celsius;
 c. cooling the base (4) of the container (2);
 d. executing a separating motion by way of which the tissue sample (1) and the holding element (3) move away from each other, the embedding medium (5) through which the holding element (3) moves during the separating motion having, during the separating motion, temperatures in the range from 54 degrees Celsius to 64 degrees Celsius, and/or those portions of the embedding medium (5) which are directly adjacent to the holding element (3) having, during the separating motion, a temperature in the range from 54 degrees Celsius to 64 degrees Celsius, wherein the separating motion ends while the holding element (3) is still located inside the embedding medium; and/or the holding element (3) is embedded together with the tissue sample (1).

22. A method for embedding a tissue sample (1) into an embedding medium, comprising:
 a. holding the tissue sample (1) in an intended orientation in a container (2) by means of a holding element (3) that presses the tissue sample (1) against a base (4) of the container (2), wherein the container (2) is part of a tissue cassette, and the tissue cassette comprises the holding element (3) that presses the tissue sample (1) against the base (4) of the container (2);
 b. pouring into the container (2) a liquid embedding medium (5) that has a temperature above 64 degrees Celsius;
 c. cooling the base (4) of the container (2);
 d. executing a separating motion by way of which the tissue sample (1) and the holding element (3) move away from each other, the embedding medium (5) through which the holding element (3) moves during the separating motion having, during the separating motion, temperatures in the range from 54 degrees Celsius to 64 degrees Celsius, and/or those portions of the embedding medium (5) which are directly adjacent to the holding element (3) having, during the separating motion, a temperature in the range from 54 degrees Celsius to 64 degrees Celsius.

23. A method for processing a tissue sample (1), comprising:
 introducing the tissue sample (1) into a container (2);
 fixing the tissue sample (1) with at least one fixing agent, and/or infiltrating the tissue sample (1) with an infiltration medium while the tissue sample (1) is located in the container (2);

keeping the tissue sample (1) in the container (2) after the fixing and/or infiltration; and block-embedding the tissue sample (1) into an embedding medium while the tissue sample (1) remains in the container (2) after the fixing and/or infiltration, wherein the block-embedding comprises:

a. holding the tissue sample (1) in an intended orientation in a container (2) by means of a holding element (3) that presses the tissue sample (1) against a base (4) of the container (2);

b. pouring into the container (2) a liquid embedding medium (5) that has a temperature above 64 degrees Celsius;

c. cooling the base (4) of the container (2); and d. executing a separating motion by way of which the tissue sample(1) and the holding element (3) move away from each other, the embedding medium (5) through which the holding element (3) moves during the separating motion having, during the separating motion, temperatures in the range from 54 degrees Celsius to 64 degrees Celsius, and/or those portions of the embedding medium (5) which are directly adjacent to the holding element (3) having, during the separating motion, a temperature in the range from 54 degrees Celsius to 64 degrees Celsius.

24. The method according to claim 23, wherein the infiltration medium is paraffin.

25. The method according to claim 23, wherein the container (2) is part of a tissue cassette and the container (2) has a base (4), and the tissue cassette comprises a holding element (3) that presses the tissue sample (1) against the base (4) of the container (2).

* * * * *